United States Patent
Bernhard

(10) Patent No.: US 10,012,626 B2
(45) Date of Patent: Jul. 3, 2018

(54) APPARATUS FOR DETERMINING A VALUE THAT REPRESENTS THE AMOUNT OF A LIQUID AND ITS USE

(71) Applicant: Endress + Hauser Conducta Gesellschaft für Mess- und Regeltechnik mbH + Co. KG, Gerlingen (DE)

(72) Inventor: Ralf Bernhard, Stuttgart (DE)

(73) Assignee: Endress+Hauser Conducta GmbH+Co. KG, Gerlingen (DE)

( * ) Notice: Subject to any disclaimer, the term of this patent is extended or adjusted under 35 U.S.C. 154(b) by 188 days.

(21) Appl. No.: 14/968,963

(22) Filed: Dec. 15, 2015

(65) Prior Publication Data

US 2016/0178425 A1 Jun. 23, 2016

(30) Foreign Application Priority Data

Dec. 17, 2014 (DE) .................. 10 2014 118 854

(51) Int. Cl.
*G01N 15/06* (2006.01)
*G01N 31/00* (2006.01)
(Continued)

(52) U.S. Cl.
CPC ......... *G01N 31/00* (2013.01); *G01F 23/2921* (2013.01); *G01F 23/2924* (2013.01); *G01F 13/00* (2013.01); *G01F 23/2927* (2013.01)

(58) Field of Classification Search
CPC ............ G01F 23/2921; G01F 23/292; G01F 23/2927; G01F 23/2922; G01F 23/2924
See application file for complete search history.

(56) References Cited

U.S. PATENT DOCUMENTS

| 4,440,022 A * | 4/1984 | Masom ............... G01F 23/2922 250/577 |
| 5,195,162 A | 3/1993 | Sultan |

(Continued)

FOREIGN PATENT DOCUMENTS

| DE | 3842480 A1 | 6/1989 |
| DE | 10221823 A1 | 11/2003 |

(Continued)

OTHER PUBLICATIONS

German Search Report, German Patent Office, Munich, dated Sep. 29, 2015.

*Primary Examiner* — Thanh Luu
(74) *Attorney, Agent, or Firm* — Mark A. Logan; PatServe

(57) ABSTRACT

An apparatus for determining a value that represents an amount of liquid in a vessel, wherein the vessel is configured to be a tube or a cuvette. The vessel for the liquid is basically transparent, with at least one radiation unit, that is arranged alongside the longitudinal axis of the vessel and that radiates light into the vessel, as well as at least one light detector with at least one light receiver that is assigned to the radiation unit and that receives the light that is coming through the vessel and forwards it to the light detector. The apparatus comprises a data processing unit that determines the value that represents the amount of the liquid in the vessel from the light that was detected by the light detector. The apparatus is characterized in that the light detector detects the sum total of the light that was radiated through the vessel and was received by all light receivers. Furthermore, the invention relates to the use of the apparatus in an analyzer.

3 Claims, 4 Drawing Sheets

(51) Int. Cl.
*G01F 23/292* (2006.01)
*G01F 13/00* (2006.01)

(56) References Cited

U.S. PATENT DOCUMENTS

| | | | | |
|---|---|---|---|---|
| 6,043,504 A | * | 3/2000 | Fujita | G01N 21/3554 |
| | | | | 250/339.12 |
| 7,473,897 B2 | | 1/2009 | Braendle | |
| 7,710,567 B1 | * | 5/2010 | Mentzer | G01F 23/2924 |
| | | | | 250/577 |

FOREIGN PATENT DOCUMENTS

| | | |
|---|---|---|
| DE | 102008016513 A1 | 10/2009 |
| JP | 61-240122 A | 10/1986 |
| WO | 03023370 A2 | 3/2003 |
| WO | 2009121567 A2 | 10/2009 |

\* cited by examiner

APPARATUS FOR DETERMINING A VALUE THAT REPRESENTS THE AMOUNT OF A LIQUID AND ITS USE

TECHNICAL FIELD

The invention relates to an apparatus for determining a value that represents the amount of a liquid in a vessel as well as its use in an analyzer.

BACKGROUND DISCUSSION

An "analyzer" in the sense of this invention shall mean a measuring apparatus in process automation engineering that measures with a wet-chemical method certain substance contents, such as, for example, the ion concentration in a medium that is to be analyzed. For that purpose, a sample is taken from the medium that is to be analyzed. Usually, the taking of the sample is performed by the analyzer itself in a fully automated fashion by means such as pumps, hoses, valves etc. For determining the substance content of a certain species, reagents that have been developed specifically for the respective substance content and that are available in the housing of the analyzer are mixed with the sample that is to be measured. A color reaction of the mixture caused in this way is subsequently measured by an appropriate measuring device, such as, for example, a photometer. To be more precise, sample and reagents are mixed in a cuvette and then optically measured with different wavelengths using the transmitted light method. Thus, the measured value is determined by the receiver based on light absorption and a stored calibration model.

In this context, it is extremely important to know the exact amount of different liquids that are being mixed with each other. For a correct determination of the substance content, it is required to precisely define the amount of the sample to be measured as well as the amount of the reagents to be mixed into it.

One possibility of measuring a certain amount of a liquid consists in filling a transparent tube 1 that has a known volume up to a certain defined fill level. It can be optically detected, when the desired fill level is reached. This is done by utilizing the fact that a filled tube possesses different refractive properties than an empty one. To do so, a light barrier with a light source and a light detector that are arranged on a tube are used. Depending on the arrangement, the received amount of light increases or decreases with the filled tube compared to the empty tube. In FIG. 1, the situation that is created with centered radiation is shown. FIG. 2 shows the conditions with eccentric radiation. In any case, the received amount of light changes depending on the tube being empty or filled. Here, setting a precise threshold value poses a problem, i.e. for determining whether the required amount of liquid has been filled in, because the refractive properties of the filled tube depend on the refractive index of the filled-in liquid. Moreover, turbidity of the liquid, dirt on the tube and deviations from the geometric ideal shape influence the value. In case of tubes with a small diameter, inaccuracies (manufacturing tolerances) in the arrangement of the components also play an important role.

SUMMARY OF THE INVENTION

The invention is based on the task of providing an arrangement that precisely determines a certain amount of medium.

The task is achieved by means of an apparatus for determining a value that represents an amount of liquid in a vessel, wherein the vessel is configured to be a tube or a cuvette wherein the. The vessel for the liquid is basically transparent, with at least one radiation unit, that is arranged alongside the longitudinal axis of the vessel and that radiates light into the vessel, as well as at least one light detector with at least one light receiver that is assigned to the radiation unit and that receives the light that is transmitted through the vessel and forwards it to the light detector wherein the. The apparatus comprises a data processing unit that determines the value that represents the amount of the liquid in the vessel from the light that was detected by the light detector. The apparatus is characterized in that the light detector detects the sum total of the light that is radiated through the vessel and received by all light receivers.

This results in minimal wiring complexity for the apparatus, i.e. the wiring between the vessel configured as a tube or a cuvette, the radiation unit, the light receiver, the light detector and the data processing unit. Moreover, the data processing unit requires only one channel for the evaluation of one of the at least one light receiver, which keeps the complexity of the circuit technology low. In addition, the measurement gets more precise and reliable.

In a first preferred variant, the apparatus comprises at least two radiation units with discrete points of radiation entry on the vessel and at least two light sources, wherein each of the at least two light sources has precisely one of the at least two radiation units assigned to it, or each of the two light sources comprises one of the at least two radiation units each, and light is being radiated at the points of radiation entry.

In a second preferred variant, the radiation unit has discrete points of radiation entry on the vessel, and the apparatus comprises at least one light source that is assigned to the radiation unit, wherein the radiation unit is designed as a light conductor, and light is radiated at the points of radiation entry.

In case of discrete points of radiation entry, several rapid signal changes of initially unknown magnitude are observed. With one first point of radiation entry, the expected value for the signal change for all other points of radiation entry can be determined. The absolute value is irrelevant.

In a third preferred variant, the radiation unit is configured as a radiation unit that continuously radiates across the longitudinal axis of the vessel, in particular, as a light conductor, and the apparatus comprises at least one light source that is assigned to the radiation unit, and the radiation unit comprises a reference section that is surrounded by sections that do not radiate light into the vessel.

In case of a continuous radiation, a continuous signal change with an initially unknown rise is observed. The rise is determined when the reference section is passed through.

Whenever the liquid column passes through a radiated section of the vessel, the sum total of the received light amount changes. This happens in any case and it is independent of whether discrete points of radiation entry are used or whether the tube is evenly penetrated by radiation over the entire length, or whether discrete points of radiation entry are realized using several light sources or only one light source that is distributed by a light conductor.

In a preferred development, when using several light sources, only identical light sources are used. This simplifies the manufacturing process and saves costs. In a preferred embodiment, the apparatus comprises at least two light receivers with discrete points of reception on the vessel and at least two light detectors, wherein each of the at least two light detectors has precisely one of the at least two light receivers assigned to it, or each of the two light detectors comprises one of the at least two light receivers each, and light is being received at the points of reception.

In a preferred variant, the light receiver has discrete points of reception on the vessel, and the light receiver is configured as a light conductor and light is being received at the points of reception.

The light receiver is the counterpart to the radiation unit: There are at least two configuration possibilities for the light receiver. In a first variant, the light receiver is designed in such a way that light can only pass through to the light detector at certain areas that are especially provided for this purpose (the points of reception). In a second variant, the light receiver comprises the light detector. In such a case, the light receiver might also comprise an optical arrangement, such as an aperture.

In a further preferred variant, the light receiver is configured as a light receiver that continuously receives light across the longitudinal axis of the vessel.

In a preferred embodiment, the light receiver or the light receivers are designed as photo diodes. A photo diode is a relatively simple and cost-effective component. A complex light receiver, such as a spectrometer, is not necessary.

The task is further achieved by using at least one apparatus, as described above, in an analyzer for determining a measured value of a measured variable in process automation engineering, in particular, for determining of at least one substance concentration, in a medium.

BRIEF DESCRIPTION OF THE DRAWINGS

The invention is further illustrated referring to the following figures. They show.

In the figures, the same features are marked with the same reference symbols.

DETAILED DESCRIPTION IN CONJUNCTION WITH THE DRAWINGS

The apparatus according to the invention is applied in an analyzer 9 in process automation engineering. The analyzer shall be described first.

To be measured is, for example, the direct absorption of a substance or the intensity of a color, which is generated by converting the substance to be determined into a color complex by means of reagents. Further possible measured variables that function according to a similar principle are turbidity, fluorescence etc. A further application example is the measuring of the chemical oxygen demand, COD, with COD being a sum parameter, which means that the measured value results from the sum total of the substances and thus, cannot be attributed to one individual substance. Further possible parameters are, for example, total carbon or total nitrogen.

Below, the concept of the invention shall be described with reference to an analyzer 9 for measuring an ion concentration, without loss of generality. In more concrete terms, the analyzer 9 measures the ammonium concentration. Other ions to be measured can be phosphate, nitrate etc.

Figure 1:
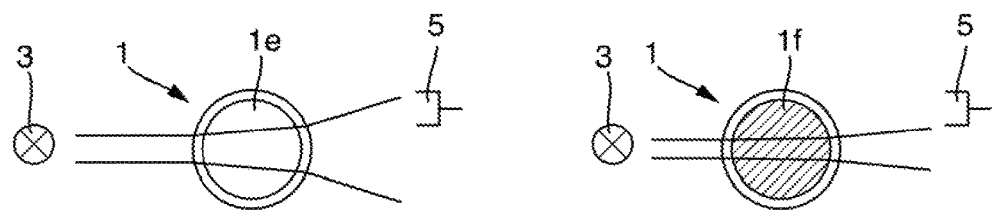
FIG. 1 is a prior art of a known measuring apparatus.
Figure 2:
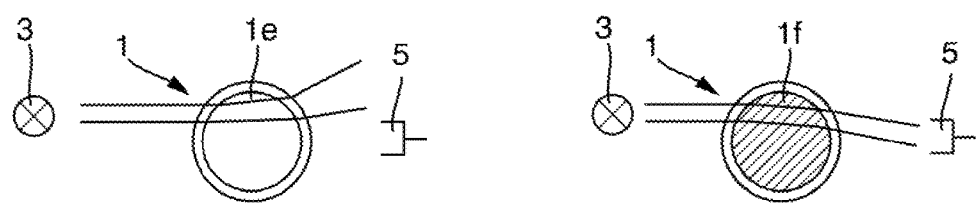
FIG. 2 is a prior art of a known measuring apparatus.
Figure 3:
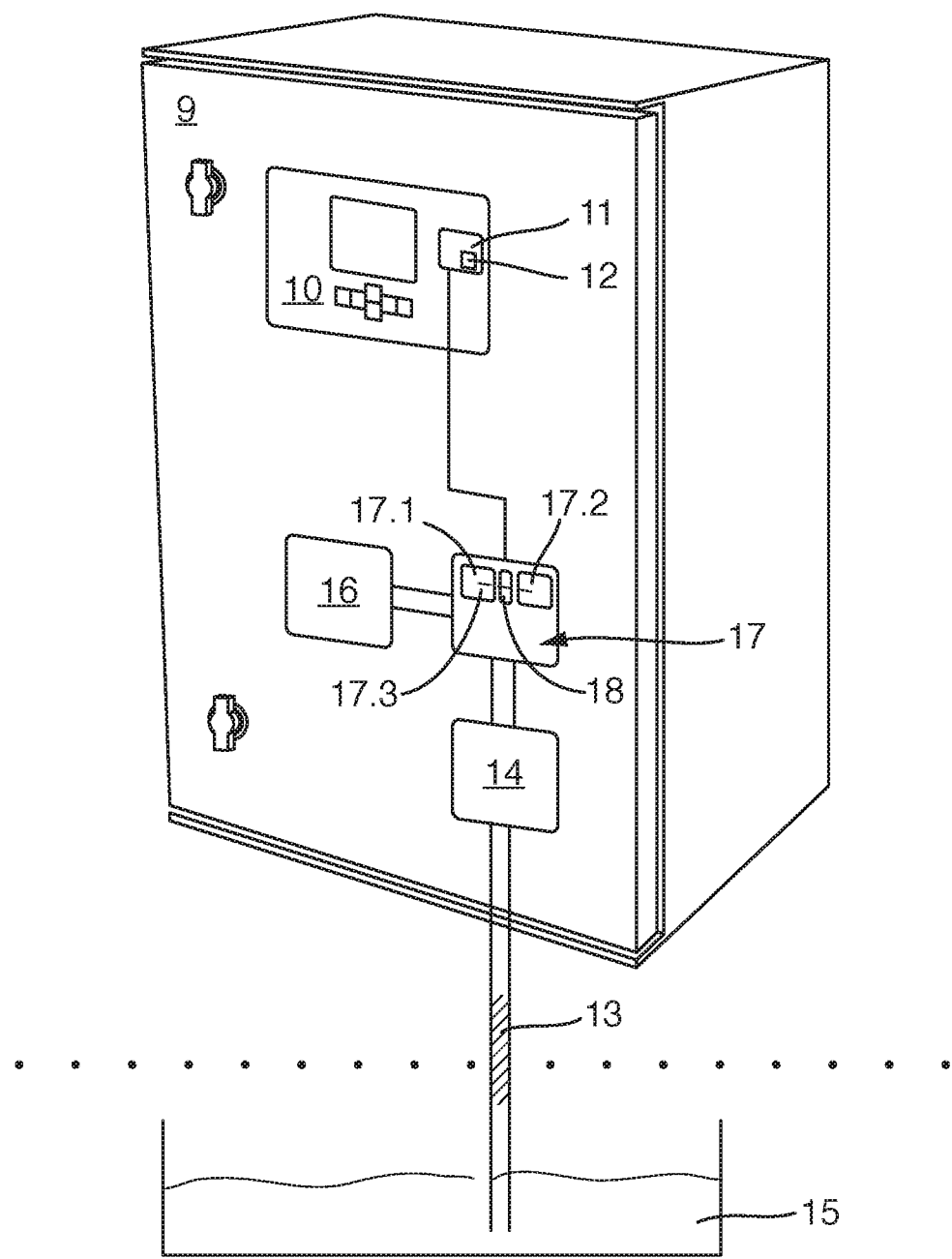
FIG. 3 is an analyzer, in which the apparatus according to the invention is sed.

A sample 13 is taken from the medium 15 that is to be analyzed, which can be a liquid or a gas, for example. Usually, the taking of the sample 13 happens fully automatically by means of subsystems 14, such as pumps, hoses, valves etc. For determining the substance content of a certain species, reagents 16 that have been developed specifically for the respective substance content and that are available in the housing of the analyzer are mixed with the sample 13 that is about to be measured. In FIG. 3, this is shown in a symbolic manner. In reality, different vessels are provided with different reagents, which are extracted by means of the aforementioned pumps, hoses and valves etc. and possibly mixed. Likewise, for every process (taking the sample, mixing of reagents etc.) separate pumps, hoses and valves can be used.

A color reaction of the mixture caused in this way is subsequently measured by an appropriate measuring device, such as, for example, a photometer 17. For that purpose, for example, the sample 13 and the reagents 16 are mixed in a cuvette 18 and optically measured with at least two different wavelengths using the transmitted light method. To that end, light is transmitted through the sample 13 by a sender 17.1. A receiver 17.2 for receiving the transmitted light is assigned to the sender 17.1, with an optical measuring path 17.3 proceeding from the sender 17.1 to the receiver 17.2 (in FIG. 3 indicated by a dotted line). Thus, the measured value is created by the receiver based on light absorption and a stored calibration feature. The sender 17.1 comprises for example one or several LEDs, i.e. one LED per wavelength or an appropriate light source with broadband stimulation. Alternatively, a broadband light source fitted with an appropriate filter is used. Typical wavelengths range from infrared to ultraviolet, i.e. from approximately 1100 nm to 200 nm. Preferably, in case of multiple light sources 3, only identical light sources are used, i.e. the light sources 3 all have the same wavelength or they are light sources with broadband stimulation of the same model.

The receiver 17.2 can comprise one or more photo diodes. A complex structured light receiver such as a spectrometer, for example, is not necessary with this invention.

Furthermore, the analyzer 9 comprises a transmitter 10 with a microcontroller 11 along with a memory 12. The analyzer 9 can be connected to a field bus via the transmitter 10. Furthermore, the analyzer 9 is controlled via the transmitter 10. Thus, the extraction of a sample 13 from the medium 15, for example, is triggered by the microcontroller 11 by sending appropriate control commands to the subsystems 14. Likewise, the measurement by the photometer 17 is controlled and regulated by the microcontroller.

The process of extracting the sample 13 is described in more detail below. For extracting the sample 13 from the medium 15, a sample extracting system (not shown) is used that can, for example, comprise a pump. Through a medium pipeline, the sample gets into a vessel 1, also referred to as dosing vessel 1 below. The dosing vessel 1 comprises one or more light barriers (see below) that serve the purpose of determining the fill level of a liquid in the vessel 1. As mentioned above, the analyzer 9 comprises liquid containers that contain reagents to be added to the sample 13 for determining the measured variable of the analyzer 9 and standard solutions for calibrating and/or adjusting the analyzer 9.

The reagents 16, or rather the containers containing the reagents 16, are connected with the dosing vessel 1 via liquid pipelines. The liquid pipelines are each capable of being shut off by a valve. The dosing vessel 1 is connected to a pump, such as a piston pump for example. The dosing vessel 1 is connected to the atmosphere via a connector and a valve. Through the valve, the dosing vessel 1 can be connected with the atmosphere. Moreover, the dosing vessel 1 is connected via a further connector with a reactor room, in the example, with the cuvette 18, which is simultaneously used for digesting the liquid sample and as a measuring cell for determining the chemical oxygen demand. The dosing vessel 1 is also connected with a waste container via the further connector. As already mentioned above, the measured variable is determined in the cuvette 18.

In the following, the dosing vessel 1 is described in more detail. The dosing vessel 1 is designed as a tube or like a cuvette. The vessel 1 is basically transparent to light coming from the light source 3 or the radiation unit 2 (see below).

Figure 4:
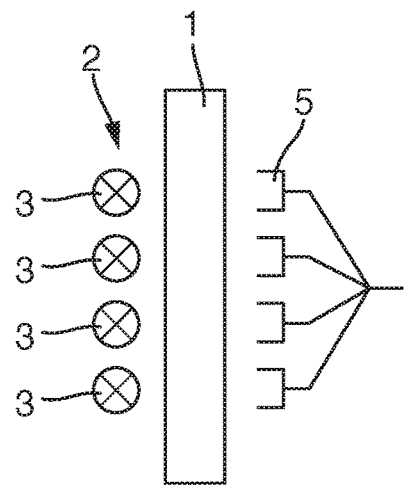
FIG. 4 is the apparatus according to the invention.
Figure 5:
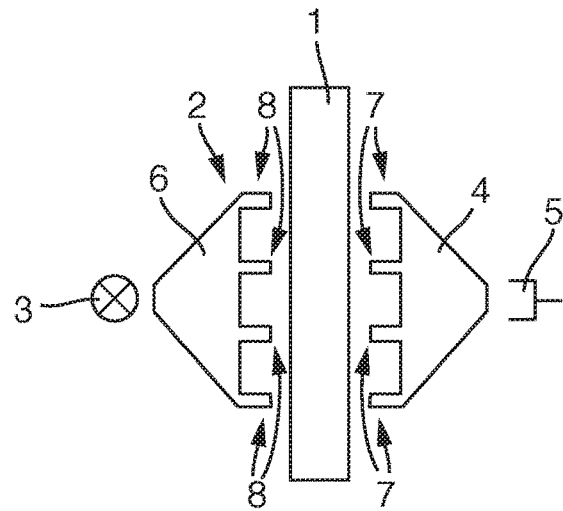
FIG. 5 is the apparatus according to the invention in one embodiment.
Figure 6:
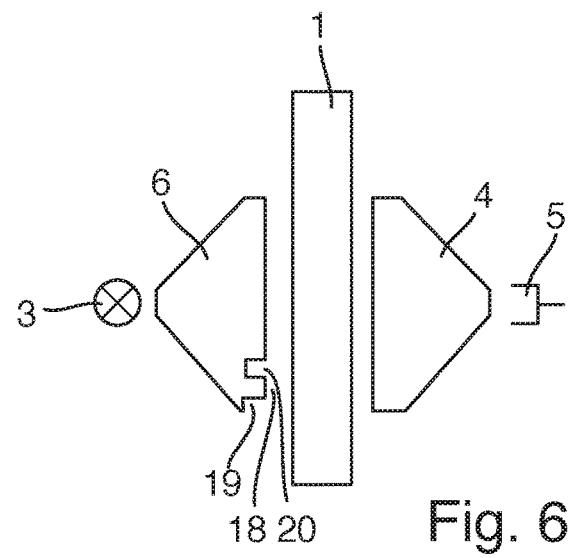
FIG. 6 is the apparatus according to the invention in a further embodiment.

In the arrangement described in FIG. 4-6, for example, the dosing vessel 1 is illuminated at several discrete points, the points of radiation entry 8, by means of at least one radiation unit 2. This is achieved, for example, by means of multiple discrete light sources 3 (e.g. LEDs), FIG. 4 shows this arrangement. In FIG. 4, four radiation units 2 with discrete points of radiation entry 8 at the vessel 1, with four light sources 3 are shown, each of the four light sources 3 being assigned to precisely one of the four radiation units 2. More precisely, each of the four light sources 3 comprises one of the four radiation units 3 each The light enters at the points of radiation entry 8. In one variant, the radiation units 2 are configured as light conductors and each light source 3 is connected with a light conductor as radiation unit 2 that sends light into the vessel 1.

Another possibility is to use only one light source 3 that is distributed via an appropriately shaped light conductor 6, as shown in FIG. 5. Here again, light is sent into the vessel at discrete points of radiation entry 8. No light enters the vessel 1, except through the points of radiation entry 8.

The sum total of the light received by all light receivers 4 is detected. This is to be explained in the following.

This is achieved, for example, by means of several light detectors 5 (e.g. photo diodes) connected in parallel, as shown in FIG. 4. More precisely, the light that is sent into the dosing vessel 1 by the radiation unit 2 is received by the light receivers 4 and forwarded to the light detectors 5. Each light detector 5 can comprise one light receiver 4, however, in FIG. 4 only the light detector 5 that comprises the light receiver 4 is shown.

Here again, a further possibility is to use a light conductor that collects the light at the desired points of reception 7 by means of the light receivers 4 and transmits it to one individual detector 5 (see FIG. 5).

Figure 7:
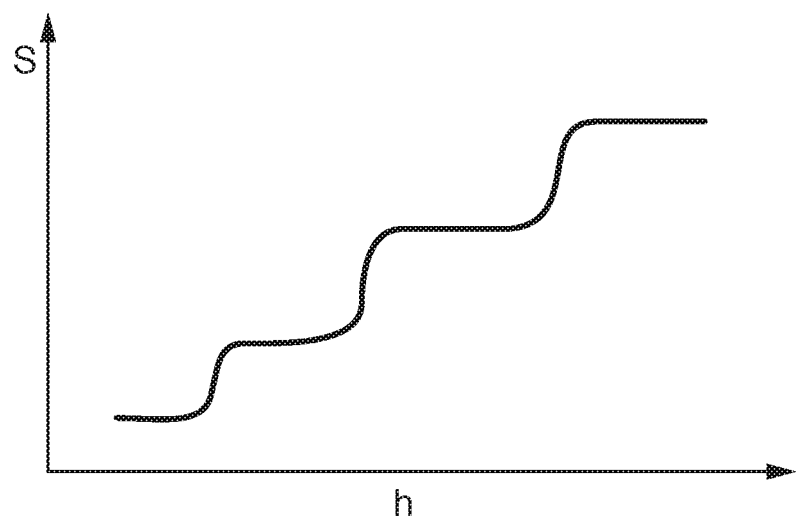
FIG. 7 shows the signal path of an apparatus according to FIG. 4 or FIG. 5.

When the dosing vessel 1 is being filled, the liquid level h passes consecutively through the different radiation units 2 or the points of radiation entry 8. Depending on the optical arrangement, the received signal S then rises or falls in steps, see FIG. 7. The first step serves as reference for the signal swing to be expected at the next steps. By counting the signal steps, the position that is currently passed through can be determined. With this method, different fill levels for dispensing can be established.

In the end, only the liquid amount matters and the fill level is detected. The liquid amount can be calculated from the known volume of the vessel 1 at a certain fill level.

For capturing the received signal S, usually amplifier electronics (not shown) with a subsequent analog/digital converter is used. The converted digital signal can then be further processed in a microprocessor e.g. by means of digital filtering, limit value observations or stage identification and stage counting.

Figure 8:
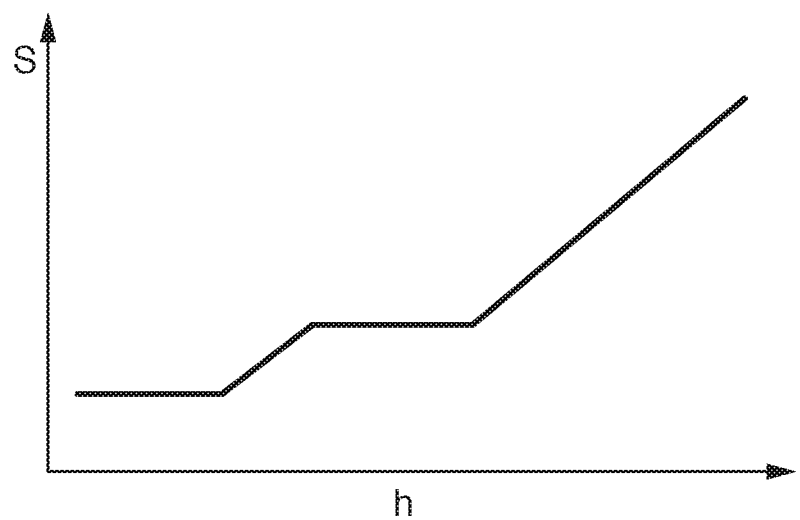
FIG. 8 shows the signal path of an apparatus according to FIG. 6.

In one embodiment, there are no discrete receiving positions, but the detection is performed integrally over the entire filling area, i.e the apparatus is configured as a radiation unit that continuously radiates light across the longitudinal axis of the vessel 1. Here, a separate area in the beginning serves as reference 18, the volume of which is known (see FIG. 6). This reference section 18 is surrounded by the sections 19 and 20 that do not radiate light into the vessel. From the signal that is generated when this reference area is passed through, a value "signal difference per volume" can then be calculated, which enables continuous dispensing (FIG. 8). However, this requires a sufficient linearity of the signal path over the entire measured distance, or the storing of an individual calibration curve.

The operating principle shall once again be explained in a summarized manner.

Whenever the fluid column h passes through an illuminated section of the vessel 1, the total received amount of light S changes. This happens in any case and is independent from whether discrete points of radiation entry 8 are used (FIGS. 4 and 5) or whether the vessel 1 is illuminated over the entire length (FIG. 6), or whether discrete points of radiation entry 8 are realized by means of multiple light sources 3 (FIG. 4) or by one light source 3 that is distributed via a light conductor 6 (FIG. 5), or whether the total received amount of light S is collected by multiple detectors 5 (FIG. 4), or collected by one light conductor 4 and transmitted to one individual detector 5 (FIG. 5), or whether it falls on one detector with a large area that covers all points of radiation entry (not shown).

The question is not, whether the amount of light changes, but how much it changes. Therefore, the value cannot be precisely predicted, as it also depends on things like misalignment, pollution, refractive index, etc. For this, different approaches are possible: Either the tube is not illuminated over the entire length but only at chosen points of radiation entry 8. Then, the received amount of light changes in steps (FIG. 7) and one only has to detect whether the value changes rapidly. The (unknown) absolute value is irrelevant. Or the vessel 1 is illuminated over the entire length. Then, the received amount of light S changes continuously with the fill level (FIG. 8). The rise, however, is initially not known. In order to determine it, the reference section 18 exists, e.g. at the bottom end of the vessel 1 (FIG. 6). The reference section 18 has a known length (hence also a known volume) and is bordered from above and below by a section 19, 20 that is not illuminated and in which nothing happens, i.e. no signal change occurs. In FIG. 8, this is represented by the two horizontal plateaus. From their difference and from the known length of the reference section 18, the unknown rise can be determined.

The invention claimed is:

1. An apparatus for determining a value that represents a liquid amount in a vessel, comprising:
   at least one light receiver;
   at least one radiation unit disposed alongside a longitudinal axis of the vessel and configured to radiate light into the vessel, the at least one radiation unit including a reference section surrounded by sections configured not to radiate light into the vessel, wherein the at least one radiation unit is embodied as a light conductor and configured to radiate light continuously across the longitudinal axis of the vessel;

at least one light source that is assigned to the at least one radiation unit;

at least one light detector; and a data processing unit configured to determine the value that represents the liquid amount in the vessel from light that was detected by the at least one light detector, wherein the vessel is configured to be a tube or a cuvette, and is essentially transparent, wherein the at least one light receiver is assigned to the at least one radiation unit, wherein the at least one light receiver is configured to receive the light that is radiated through the vessel and to forward the light to the at least one light detector, and wherein the at least one light detector is configured to detect the sum total of the light that was radiated through the vessel and was received by all light receivers.

2. The apparatus of claim 1, wherein the at least one light receiver is configured to receive light continuously across the longitudinal axis of the vessel.

3. The apparatus of claim 1, wherein the at least one light detector is a photodiode.

\* \* \* \* \*